US010744019B2

(12) United States Patent
Omarsson et al.

(10) Patent No.: US 10,744,019 B2
(45) Date of Patent: Aug. 18, 2020

(54) ORTHOPEDIC DEVICE FOR TREATING DROP FOOT AND METHOD FOR USING THE SAME

(71) Applicant: Ossur Iceland ehf, Reykjavik (IS)

(72) Inventors: Bjorn Omarsson, Reykjavik (IS); Hronn Kristinsdottir, Reykjavik (IS); Liza Boon, Reykjavik (IS); Marcel Jansen, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 396 days.

(21) Appl. No.: 15/674,715

(22) Filed: Aug. 11, 2017

(65) Prior Publication Data
US 2018/0042752 A1    Feb. 15, 2018

Related U.S. Application Data

(60) Provisional application No. 62/373,814, filed on Aug. 11, 2016.

(51) Int. Cl.
*A61F 5/01* (2006.01)

(52) U.S. Cl.
CPC .......... *A61F 5/0113* (2013.01); *A61F 5/0102* (2013.01); *A61F 5/0127* (2013.01)

(58) Field of Classification Search
CPC .... A61F 5/0113; A61F 5/0111; A61F 5/0102; A61F 5/0127; A61F 5/01
USPC .......................................................... 602/28
See application file for complete search history.

(56) References Cited

U.S. PATENT DOCUMENTS

| 2,477,591 | A | | 8/1949 | Follis |
| 2,663,294 | A | | 12/1953 | Harrison |
| 2,717,387 | A | | 9/1955 | McMahan |
| 2,733,443 | A | | 2/1956 | Holder |
| 3,527,209 | A | * | 9/1970 | Baker .................... A61F 5/0113 |
| | | | | 602/28 |
| 4,273,328 | A | | 6/1981 | Ozbey et al. |
| 4,329,982 | A | | 5/1982 | Heaney |
| 4,556,054 | A | * | 12/1985 | Paulseth ............... A61F 5/0111 |
| | | | | 602/27 |

(Continued)

FOREIGN PATENT DOCUMENTS

| DE | 327817 C | 10/1920 |
| DE | 1970630 U | 10/1967 |

(Continued)

OTHER PUBLICATIONS

International Search Report from PCT Application No. PCT/US2017/046451, dated Nov. 13, 2017.

*Primary Examiner* — Tarla R Patel
(74) *Attorney, Agent, or Firm* — Workman Nydegger

(57) ABSTRACT

An orthopedic device is arranged as a lightweight ankle-foot orthosis providing dynamic support for drop foot or related disorders requiring dorsiflexion. The orthopedic device includes a main support adapted to secure about a lower leg, a strap assembly having a first portion coupling to the main support, and a second portion arranged to be drawn therefrom, and an anchor for receiving and attaching to the second portion of the strap assembly. The location of the anchor along a foot component enables increased medial-lateral control, and the arrangement of the strap assembly permits dorsiflexion during swing phase of a user's gait.

14 Claims, 9 Drawing Sheets

(56) References Cited

U.S. PATENT DOCUMENTS

| | | | |
|---|---|---|---|
| 4,559,934 A | 12/1985 | Philipp | |
| 4,651,723 A | 3/1987 | Satoh | |
| 4,829,982 A | 5/1989 | Abidor | |
| 5,088,480 A | 2/1992 | Wang | |
| 5,135,217 A | 8/1992 | Swain | |
| 5,277,699 A * | 1/1994 | Williamson | A61F 5/0118 128/882 |
| 5,297,294 A | 3/1994 | Washick | |
| 5,813,955 A | 9/1998 | Gutkowski et al. | |
| 5,860,423 A * | 1/1999 | Thompson | A61F 5/0113 128/882 |
| 5,898,939 A | 5/1999 | Schramm | |
| 6,178,555 B1 | 1/2001 | Williams | |
| 6,602,217 B2 | 8/2003 | Crawford et al. | |
| 6,955,616 B1 | 10/2005 | Barth et al. | |
| 7,094,213 B1 * | 8/2006 | Cook | A61F 13/065 36/140 |
| 7,153,246 B2 | 12/2006 | Koscielny et al. | |
| 7,179,206 B2 | 2/2007 | Backes et al. | |
| 8,353,807 B2 | 1/2013 | Kruijsen et al. | |
| 8,480,546 B2 * | 7/2013 | Spencer | A43B 7/00 482/44 |
| 8,556,839 B2 * | 10/2013 | Caldwell | A61F 5/0113 602/16 |
| 2003/0040408 A1 | 2/2003 | Cooper, Sr. | |
| 2005/0070833 A1 * | 3/2005 | Shields | A61F 5/0113 602/27 |
| 2005/0126047 A1 * | 6/2005 | Kruijsen | A61F 5/0113 36/118.5 |
| 2010/0324463 A1 * | 12/2010 | Klotz | A61F 5/0113 602/28 |
| 2011/0082404 A1 * | 4/2011 | Wenger | A61F 5/0111 602/28 |
| 2012/0065564 A1 * | 3/2012 | Hoffmeier | A61F 5/0113 602/28 |
| 2012/0209163 A1 | 8/2012 | Phillips | |
| 2015/0045709 A1 * | 2/2015 | Wiley | A61F 5/0111 602/28 |
| 2015/0265450 A1 * | 9/2015 | Rodgers | A61F 5/0127 601/84 |
| 2016/0015545 A1 | 1/2016 | Petursson | |
| 2016/0067075 A1 * | 3/2016 | Malinowski | A61F 5/0113 602/28 |
| 2016/0095735 A1 * | 4/2016 | Wenger | A61F 5/0127 602/28 |
| 2016/0220409 A1 | 8/2016 | Romo et al. | |

FOREIGN PATENT DOCUMENTS

| | | |
|---|---|---|
| FR | 2586907 A3 | 3/1987 |
| WO | 0135876 A1 | 5/2001 |

\* cited by examiner

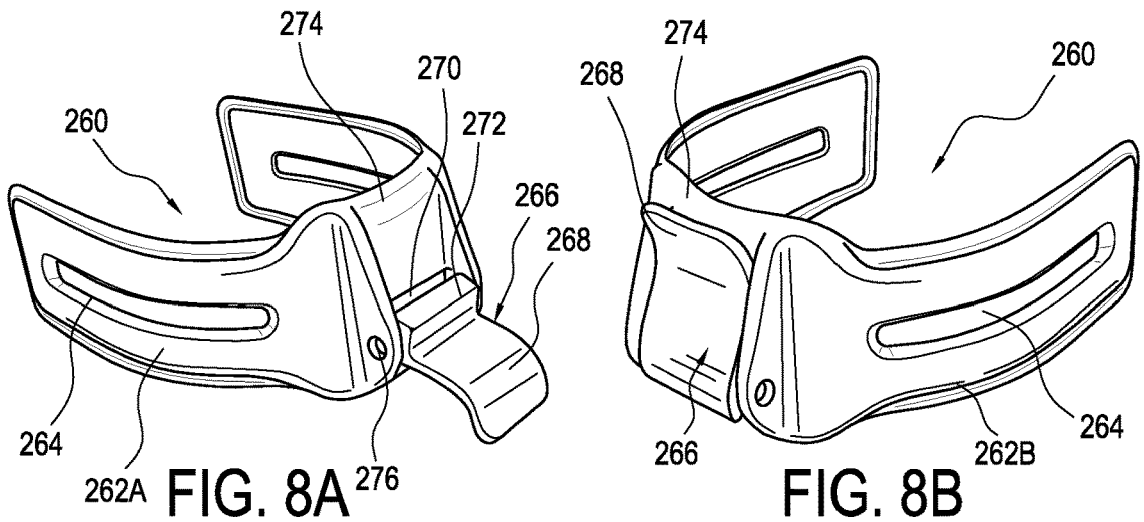
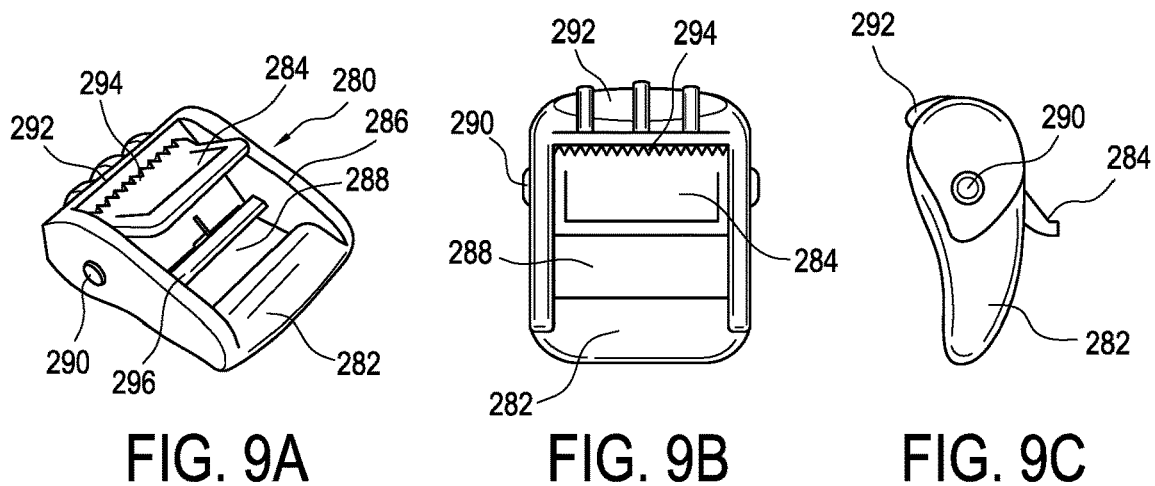
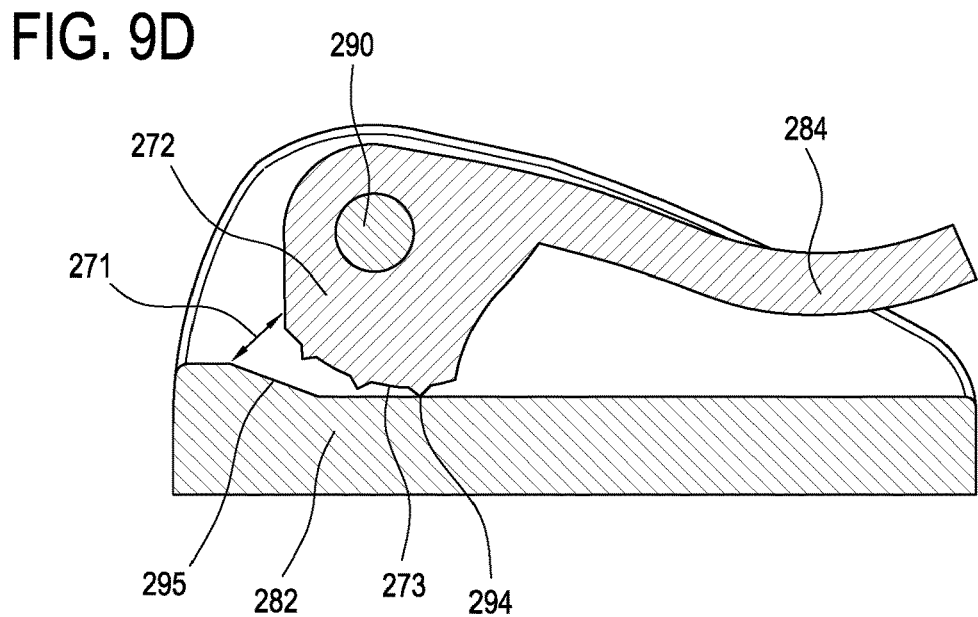

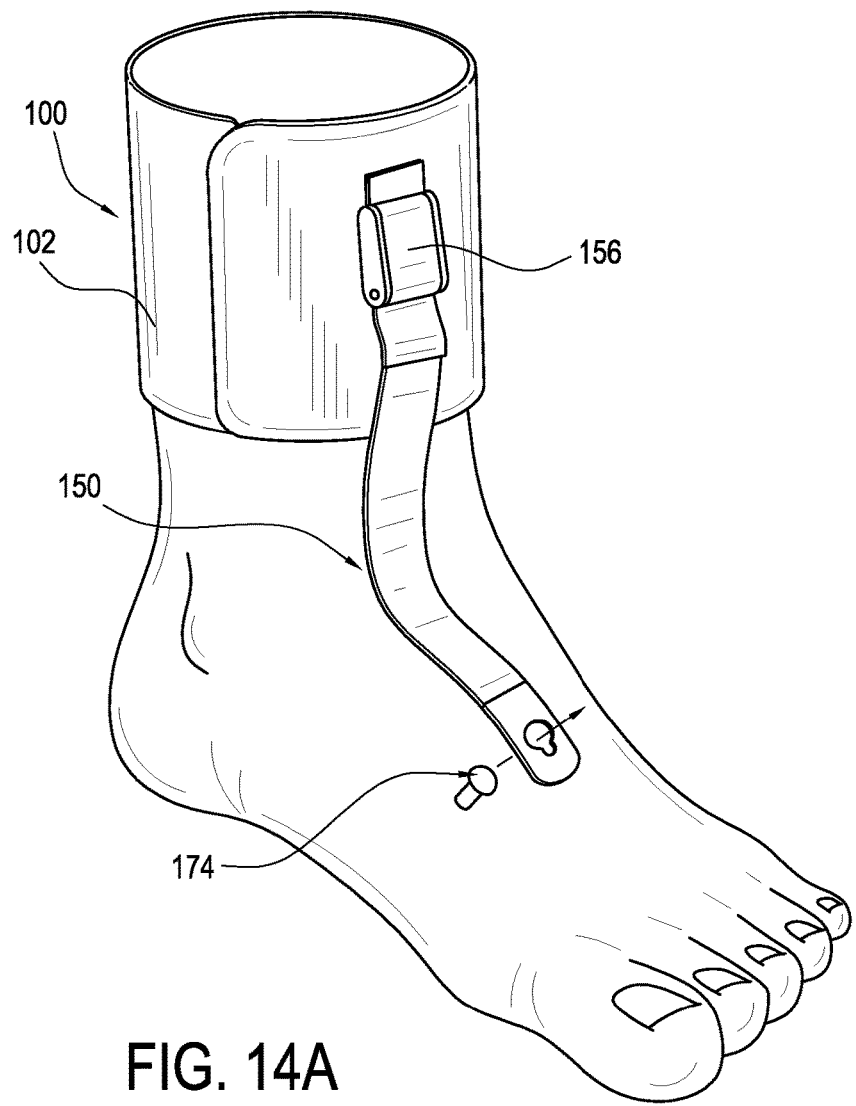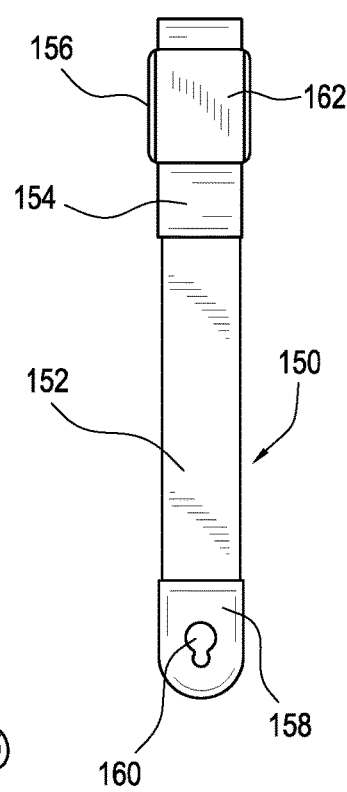
FIG. 14A
FIG. 14B

ORTHOPEDIC DEVICE FOR TREATING DROP FOOT AND METHOD FOR USING THE SAME

FIELD OF THE DISCLOSURE

The disclosure relates to an orthopedic device including an assembly for supporting a foot-drop affected foot relative to a lower leg belonging to the foot such that the foot is prevented from dropping down relative to the lower leg when the foot is raised by the lower leg from a supporting surface.

BACKGROUND

Drop foot is a gait abnormality in which the forefoot drops due to weakness, irritation, or damage to the common fibular nerve including the sciatic nerve, or paralysis of the muscles in the anterior portion of the lower leg. Drop foot may be characterized by an inability or impairment to raise the toes or a foot relative to an ankle in dorsiflexion, or inversion or eversion of the foot. The foot hangs with toes pointing down, causing the toes to scrape the ground while walking, and requiring the individual to lift the corresponding leg higher than normal when walking to avoid slapping the foot on the ground. Drop foot is highly pronounced in the part of the gait cycle that involves the most dorsiflexion, such as at heel contact and during the swing phase.

Drop foot may be temporary or permanent depending on muscle weakness or nerve damage or impairment, and most commonly affects one side only although it can affect both sides, either equally or to different degrees.

Drop foot can be caused by nerve damage alone or by muscle or spinal cord trauma, neurological dysfunction, abnormal anatomy, complications relating to surgery (i.e., hip or knee), or disease. Diseases that can cause drop foot include direct hit to posterolateral neck of fibula stroke, amyotrophic lateral sclerosis (ALS or Lou Gehrig's Disease), muscular dystrophy, Charcot Marie Tooth disease, multiple sclerosis, cerebral palsy, hereditary spastic paraplegia and Friedreich's ataxia.

Ankle-foot orthoses may treat drop foot by controlling the position and motion of the ankle. An ankle-foot orthosis may be constructed from plastic and possess the shape of an "L" with the upright portion behind the calf and the lower portion running underneath the foot. Alternatives may include jointed ankles and may provide different control. These alternative ankle-foot orthoses are often custom formed and are bulky, particularly when worn with clothing and shoes.

In a prior art orthopedic device in FIGS. 1A and 1B, drop foot orthosis 2 is provided with a first attachment member or ankle component 4 for attachment of the drop foot orthosis 2 to the lower leg, a second attachment member or foot component 6 for attachment of the drop foot orthosis 2 to an upper side or instep of a shoe 8 enclosing the foot-drop affected foot, and a strap assembly joining the first and second attachment members 4, 6. The second attachment member 6 is provided with an attachment plate or inlay 7 which, in use, is positioned under the upper part or instep (such as a tongue, shoe lace or edge) of the shoe 8 (see FIG. 1B). The user, when walking, experiences an upward (supporting) force 36 which acts on a point near the tongue 34 of the shoe 8.

This assembly requires careful placement of the plate 7, and is generally limited to shoes having laces. The plate 7 may slide about within the shoe 8 as a user walks, and may not offer a stable connection if the shoe laces are not sufficiently tensioned. It may prove cumbersome for attaching and detaching the plate 7, particularly if the plate 7 slides about. It also precludes easy and/or one-handed adjustment. This assembly further fails to offer a user the option to adjust the orthopedic device to provide more or less medial or lateral support, as their specific condition may require. The assembly also makes it difficult to replace the strap, adjust the length of the strap to match an individual's dimensions, or to switch out the strap and plate for a different preferable strap and/or foot component or attachment.

Another problem with this assembly is that it does not allow for voluntary plantar flexion or other articulation by a user during the swing phase or provide dorsiflexion support. This reduces comfort and desirability for long-term use.

Existing strap attachment and adjustment mechanisms are frequently inadequate for holding a strap in position due to undesired slippage of the strap. This is at least in part due to most adjustment mechanisms providing a lever with a flat profile. In these devices, a component of the strap force creates a clearance between the strap attachment mechanism and lever face. Manufacturing variability also affects the ability to properly hold a strap in place without undesired slippage.

From the foregoing, there is a need for an orthopedic device that provides improved attachment between ankle and foot components, while offering better medial and/or lateral support and flexibility and ease of use.

SUMMARY

A lightweight orthopedic device serves as an ankle-foot orthosis providing dynamic support for drop foot or related disorders. The orthopedic device assists in gait improvement by providing support the moment the foot is raised by generating an upward, supporting force. The orthopedic device is simple to fit, and is arranged to be generally invisible when worn with or without a shoe.

The orthopedic device may include an ergonomic ankle component and a strap assembly arranged to attach to a shoe or a foot component with or without a shoe. The strap assembly attaches to the ankle component and is releasably connected to both the ankle component and the shoe or foot component. An anchor is installable on a shoe and can be located centrally, laterally, or medially on the shoe or foot component. The orthopedic device offers dorsiflexion during swing phase of a user's gait, increases postural stability, and allows for voluntary plantar flexion. Due to its construction, the orthopedic device can be donned and doffed with one hand, and can be worn comfortably, due to the construction of the ankle and foot components, for extended periods of time.

In an embodiment of the orthopedic device, a main support is adapted to secure about a lower leg, a strap assembly has a first portion coupling to the main support, and a second portion is arranged to be drawn therefrom, and an anchor receives and attaches to the second portion of the strap assembly.

A foot component may be provided to secure about the lower leg of a user and the anchor is secured to the foot component. The foot component may define at least two apertures among which the anchor is selectively secured to the foot component. The foot component may include at least two straps extending from a main portion of the foot component, and the at least two straps define a clearance therebetween and over the main portion at which the anchor is secured.

The strap assembly may be releasably attached to the anchor and adjustable in length at the first portion relative to the main support. An attachment component may be secured to the main support such that the first portion of the strap assembly couples to the attachment component. The attachment component comprises a lever device arranged to grasp the first portion of the strap assembly.

An end of the first portion may define a tab extending from a first end of the attachment component, and the first portion extends through the attachment component and from a second end of the attachment component towards the anchor.

The strap assembly preferably includes a main segment and at least one elastic segment attached to the main segment. The main segment can be substantially less elastic than the at least one elastic segment, or simply inelastic relative to the at least one elastic segment. The at least one elastic segment may include at least two elastic segments parallel and generally coextensive with one another. The main segment may have a first end from which a tab extends and a second end at which a first end of the at least one elastic segment secures.

A second end of the at least one elastic segment preferably carries a coupling part securable to the anchor. The coupling part may define a keyhole adapted to receive a head of the anchor and lockingly engage a shaft extending from the head due to bias of the at least one elastic segment pulling the coupling part toward the leg support.

The main support preferably defines a curved shape arranged as semi-rigid or rigid to resiliently maintain its shape between donning and doffing.

In an exemplary method for donning an orthopedic device, steps may include securing a main support about a lower leg; coupling a first portion of a strap assembly to the main support; and extending and securing a second portion of the strap assembly to an anchor. The anchor may be configured to be adjustable relative to a neutral strap assembly orientation, such that the strap assembly extends at a non-parallel angle between the main support and the anchor relative to the neutral orientation. The anchor may be securable to a foot component which is securable to a foot. The length of the strap assembly may be adjusted between the main support and the anchor by adjusting the first portion of the strap assembly relative to the main support.

These and other features, aspects, and advantages of the present disclosure will become better understood regarding the following description, appended claims, and accompanying drawings.

BRIEF DESCRIPTION OF THE DRAWINGS

FIG. 8A is a perspective view of an embodiment of an attachment component in the ankle component of FIG. 7 showing a lever in an unsecured setting.

FIG. 8B is another perspective view of the attachment component of FIG. 8A in a secured setting.

FIG. 9A is a perspective view of another embodiment of an attachment component.

FIG. 9B is a front elevational view of the attachment component in FIG. 9A.

FIG. 9C is a side elevational view of the attachment component in FIG. 9A.

FIG. 9D is a side elevational view of an embodiment of an attachment component.

FIG. 14A is a perspective view of the ankle component of FIG. 2 placed on an ankle of a user and a strap assembly attached thereto.

FIG. 14B is an elevational view of the strap assembly in FIG. 14A.

Figure 1A:
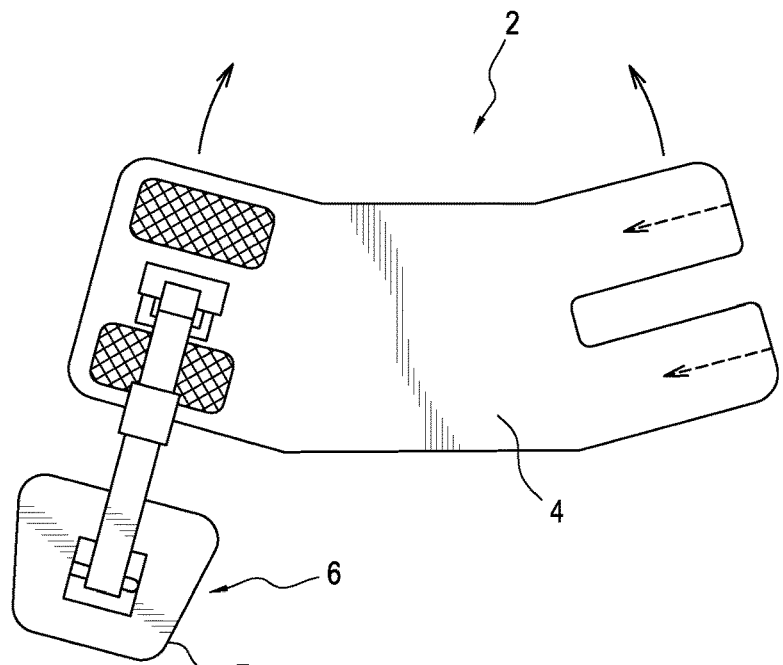
FIG. 1A is a schematic perspective representation of a prior art orthopedic device arranged for treating drop foot.

The drawing figures are not drawn to scale, but instead are drawn to provide a better understanding of the components, and are not intended to be limiting in scope, but to provide exemplary illustrations.

DETAILED DESCRIPTION OF VARIOUS EMBODIMENTS OF THE DISCLOSURE

Figure 1B:
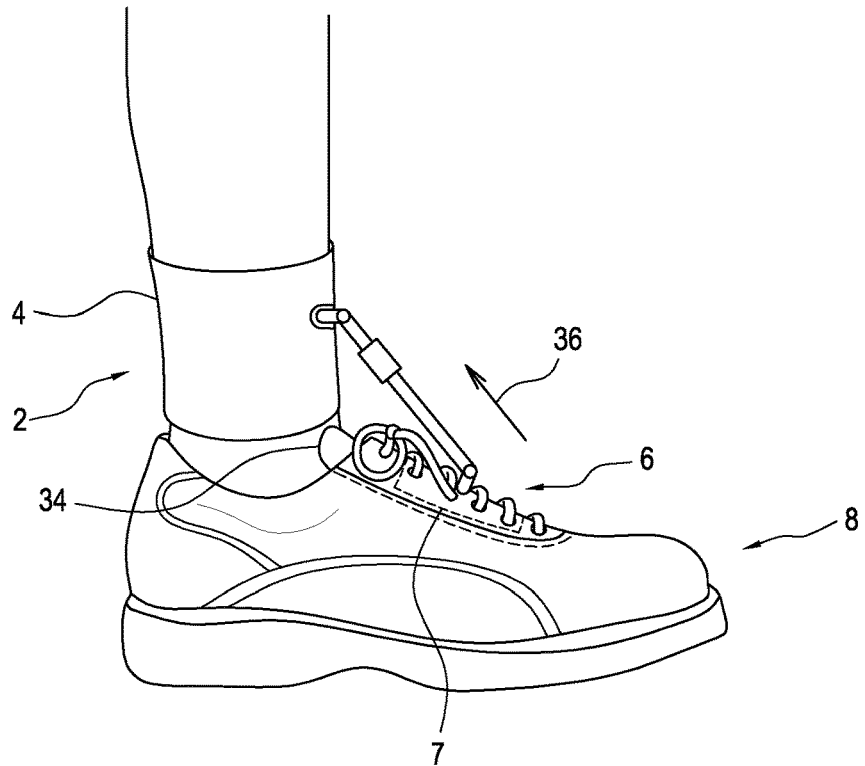
FIG. 1B is a schematic perspective side view of the prior art device of FIG. 1A placed on a foot and ankle of a person in combination with a shoe.

The orthopedic device embodiments disclosed herein are improvements over the prior art orthopedic device in a drop foot orthosis in FIGS. 1A and 1B.

Figure 2:
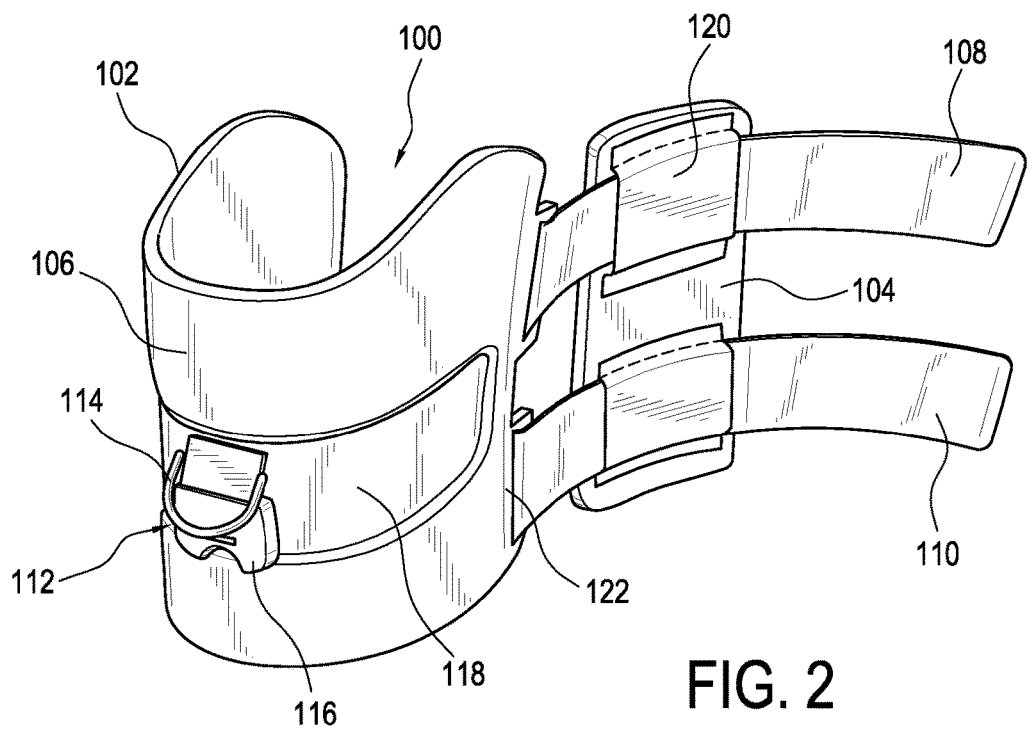
FIG. 2 is a perspective view of an ankle component of an embodiment of the orthopedic device in a curved, contoured configuration.

FIG. 2 shows an exemplary ankle component 100 in an embodiment drop foot or ankle-foot orthosis. The ankle component 100 includes a main support 102, a supplementary support 104 and at least one strap, for example first and second straps 108, 110 depending from the main support 102 and retained by the supplementary support 104. The main support 102 is adapted to extend about the lower leg such as the anterior ankle or shin of the user above the foot. The supplementary support 104 may be slidable along the at least one strap 108, 110, and tensionable along the lower leg, such as at the posterior ankle. The at least one strap 108, 110 is adapted to extend circumferentially about the lower leg in combination with the main support 102.

The at least one strap 108, 110 is advantageous in that main support 102 may be formed from a foam laminated Nylon/spandex with loop material, and the at least one strap 108, 110 preferably having hook material is not limited to where they are secured on the main support 102. The at least one strap 108, 110 may be formed similarly to the main support 102 so that if necessary, the hook of the at least one strap 108, 110 can secure to an opposite surface defining loop material.

The main support 102 may be adapted to form a curved shape, such as a U-shape. The U-shape is arranged to be clamped to the ankle to enable one-handed donning. The ankle component 100 may be semi-rigid or rigid, and particularly arranged as being resilient to generally maintain its curved shape over repeated donning.

The main support 102 may be contourable to adapt to the anatomy of a user, as in the shape of the anterior ankle or shin. The main support 102 may include malleable aluminum or other suitable materials and stay elements for facilitating bending and adapting to an individual anatomy but sufficiently strong to hold its contoured shape. In this example, a center portion 118 may comprise the malleable material. The center portion 118 may comprise injection molded plastic preformed to impart the curvature to the main support 102. The center portion 118 may be resilient and conform to the shape of the user's lower leg upon tightening of the at least one strap 108, 110.

Figure 3:
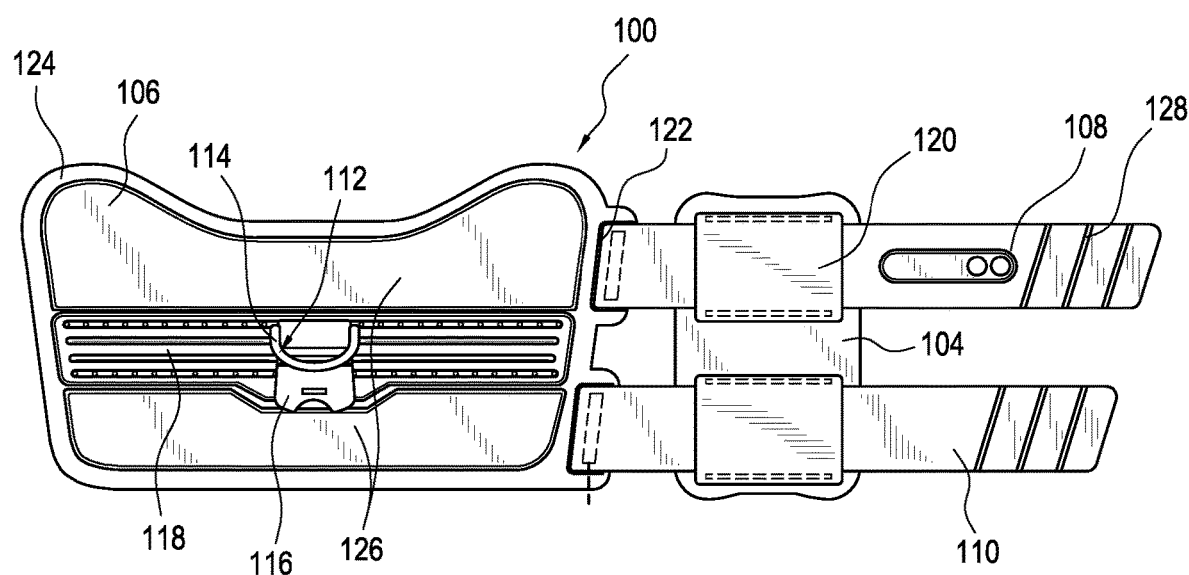
FIG. 3 is a plan view of the ankle component of FIG. 2 in a flat, non-contoured configuration.

Referring to FIGS. 2 and 3, the main support 102 includes a frame portion 106 adapted to preferably extend generously about the lower ankle for securely holding into position on the lower leg and preventing migration on the lower leg. The main support 102 includes a strap attachment 112 for a coupling strap connecting to a shoe, defined in more detail in FIGS. 4A-4B. The strap attachment 112 may include a strap loop 114, or a buckle 116 or both for coupling to the coupling strap. The strap attachment 112 attachment is preferably centrally located on the main support 102, particularly at the apex of the curved shape.

The main support 102 preferably includes panels 126 which are hook-receivable for engagement with the straps 108, 110. The main support 102 may have edging 124 located about its periphery for providing a relaxed fit and distributing pressure about the lower leg of the user. The edging 124 may comprise a softer material than material forming the frame portion 106.

The supplementary support 104 preferably defines channels 120 through which the straps 108, 110 may extend from attachment slots 122 defined by the main support 102 upon which first ends of the straps 108, 110 secure. Second ends of the straps 108, 110 are securable to the panels 126. The supplementary support 104 may comprise a pad for placement over the Achilles heel. Preferably, the supplementary support 104 comprises EVA or open-cell foam, and the channels 120 are formed by fabric sewn or otherwise secured to the foam.

The straps 108, 110 are preferably formed from back to back velours to provide a soft and comfortable fit for the user. The second ends of the straps 108, 110 may comprise ultrasonic welding lines 128 for ease in trimming to length and adapting to the shape of the user's lower leg. The second ends of the straps 108, 110 may also include hook material for securing to the panels 126.

Figure 4:
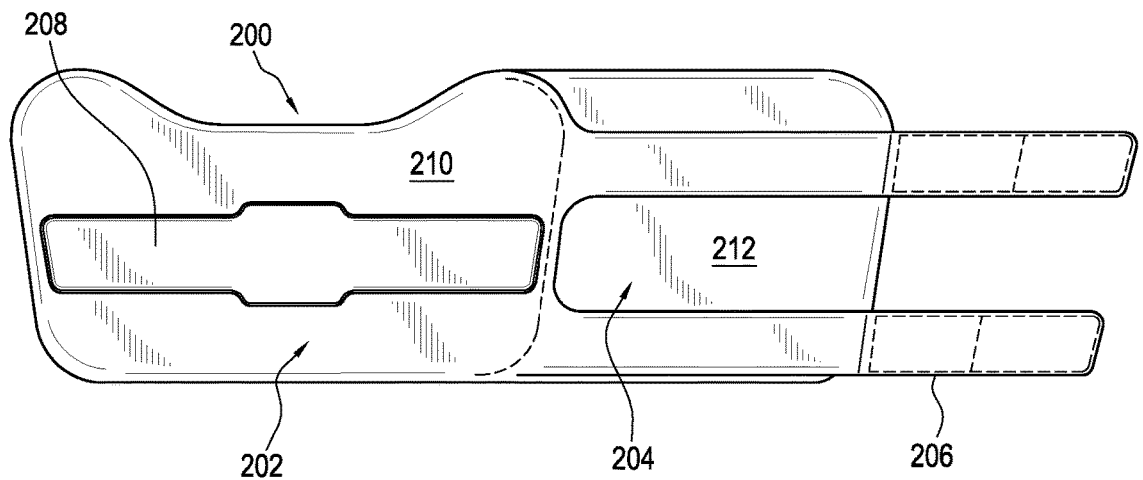
FIG. 4 is a plan view of another ankle component embodiment of an orthopedic device in a flat, non-contoured configuration showing an outer side.
Figure 5:
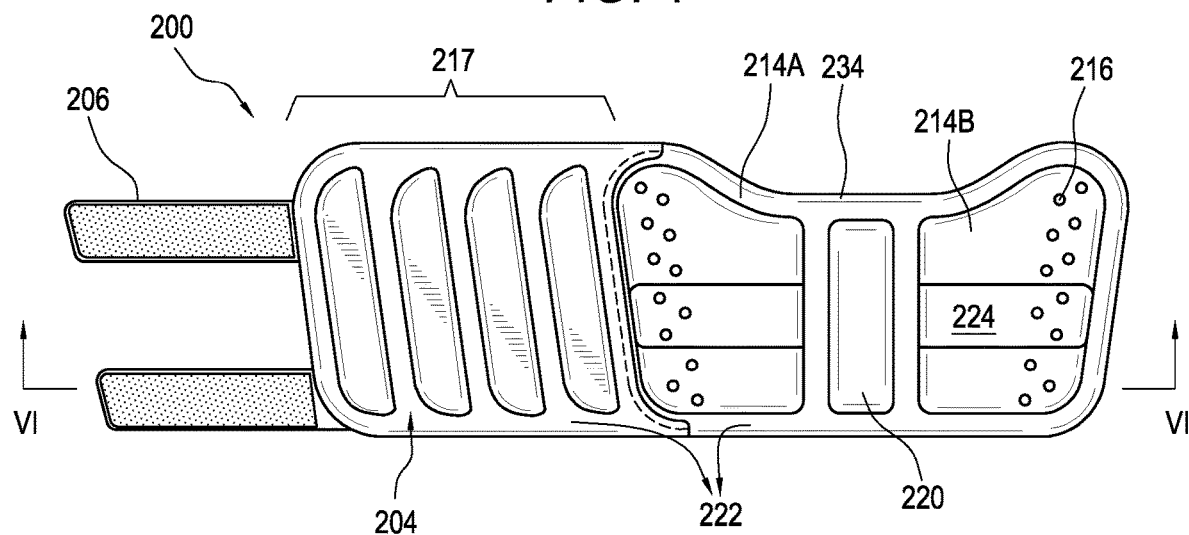
FIG. 5 is a plan view of the ankle component of FIG. 4 showing an inner side.
Figure 6:
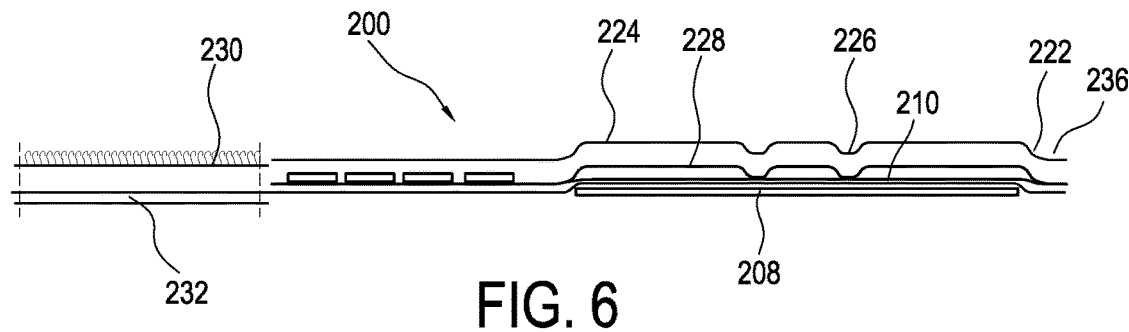
FIG. 6 is a cross-sectional view taken along line VI-VI of the ankle component of FIG. 5.

Turning to the embodiment of FIGS. 4-6, the ankle component 200 includes a main support 202 and a supplementary support 204 extending from the main support 202.

At least one strap 206 extends from the main support 202, and may comprise multiple straps, as shown. As the device is donned, the main support 202, having a curved shape as previously described, forms around the ankle and stays in place relatively stable. As the at least one strap 206 is wrapped around the ankle to attach to the main support 202, and the supplementary support 204 is secured to the ankle between the at least one strap 206 and the skin. The main support 202 defines a debossed or recessed section 208 adapted to receive a strap attachment device (as better shown in FIGS. 7-8B).

The ankle component 200 has padded sections spaced apart by non-padded sections. The main support 202 includes pads whereby first and second side pads 214A, 214B spaced apart by a central pad 220 generally aligned with a central notched portion 234 of the main support 202 defined along its upper edge. The central notched portion 234 is configured and dimensioned to generally accommodate a user's shin or tibia, along with the central pad 220 which is adapted to align with a user's tibia. The first and second side pads 214A, 214B are arranged to firmly embrace side portions, of at least an anterior side of the lower leg, when the ankle component 200 is wrapped about the user's leg.

The pads are spaced apart by welded areas 222 defined as thinner regions of the main component as compared to the pads, whereby the foam or other compressible material forming the pads is reduced or compressed in the welded areas 222. Notches 226 may be formed along the welded areas 222 to provided better conformability of the ankle component 200 to a user's leg. The welded areas 222 define edge portions 236 generally devoid of padding material for close fitting about the periphery of the ankle component 200 on the leg of the user. The supplemental support 204 likewise includes a plurality of pads 217 generally arranged in a series. In variations of the ankle component 200, any of the pads or padding areas may be removed and/or the layers forming the ankle component 200 may have padding properties.

As exemplified in FIG. 5, traction elements 216 may be provided over at least the pads 217 for preventing migration on the leg of the user, particularly in combination with the at least one strap 206 when it is tensioned about the leg of the user. The traction elements 216 may be formed by silicone or other suitable material providing sufficient traction against skin or clothing of a user, and be arranged in a pattern to enhance migration control while enabling suitable comfort and breathability for the ankle component 200. The traction elements 216 may be glued or applied directly to the surface of the liner 224, and integrated therewith to remain on the ankle component 200 due to repeated donning and doffing, and wearing of the ankle component 200.

FIG. 6 exemplifies a cross-section of the ankle component 200, and the material layers preferably used to construct the ankle component 200 according to the embodiments of FIGS. 4 and 5. Specifically, a soft and breathable fabric-based outer liner 210 is used on the outer side of the of the ankle component 200, and may be formed by a hook-receivable material such as a velours. In this embodiment, an open cell foam 228 is preferably used as a padding layer between the outer liner 210, and a soft and breathable fabric-based inner liner 224. The padding areas 214A, 214B, 216, 220, are spaced apart from one another by the welded areas 222, inclusive of notches 226 formed between certain padding areas 214A, 214B, 216. An outer side of the supplementary support 204 comprises additional padding material 212.

The at least one strap 206 may comprise inner and outer layers 230, 232, whereby the inner layer 230 may include hook material adapted to securing interconnect with the hook-receivable material of the outer liner 210. The outer layer 232 may comprise soft, breathable material, or may comprise the combination of the inner and outer liners 210, 224 with the inner layer 230 bearing the hook material thereon. If there are two straps, as shown in FIG. 4, the straps 206 are separated by a distance defined by a height of the debossed section 208 so that the straps 206 secure above and below an attachment component, as discussed referring to FIG. 7, and can engage with the outer liner 210.

By way of the arrangement of the liners and padding, and the further configuration of the padding areas, the ankle component enables enhanced conformability to different users' anatomy. The liner construction is low profile in part due to the welded areas, thereby reducing material thickness in areas where it is less required or minimizing padding. The welded areas further contribute to improved conformability by the notches which may be formed from thermoforming involving compressed areas of the padding. Thermoforming can also arrange the pattern of the pads into more ergonomic arrangements better accommodating an ankle than a foam layer having a single thickness generally across the entire ankle component.

Figure 7:
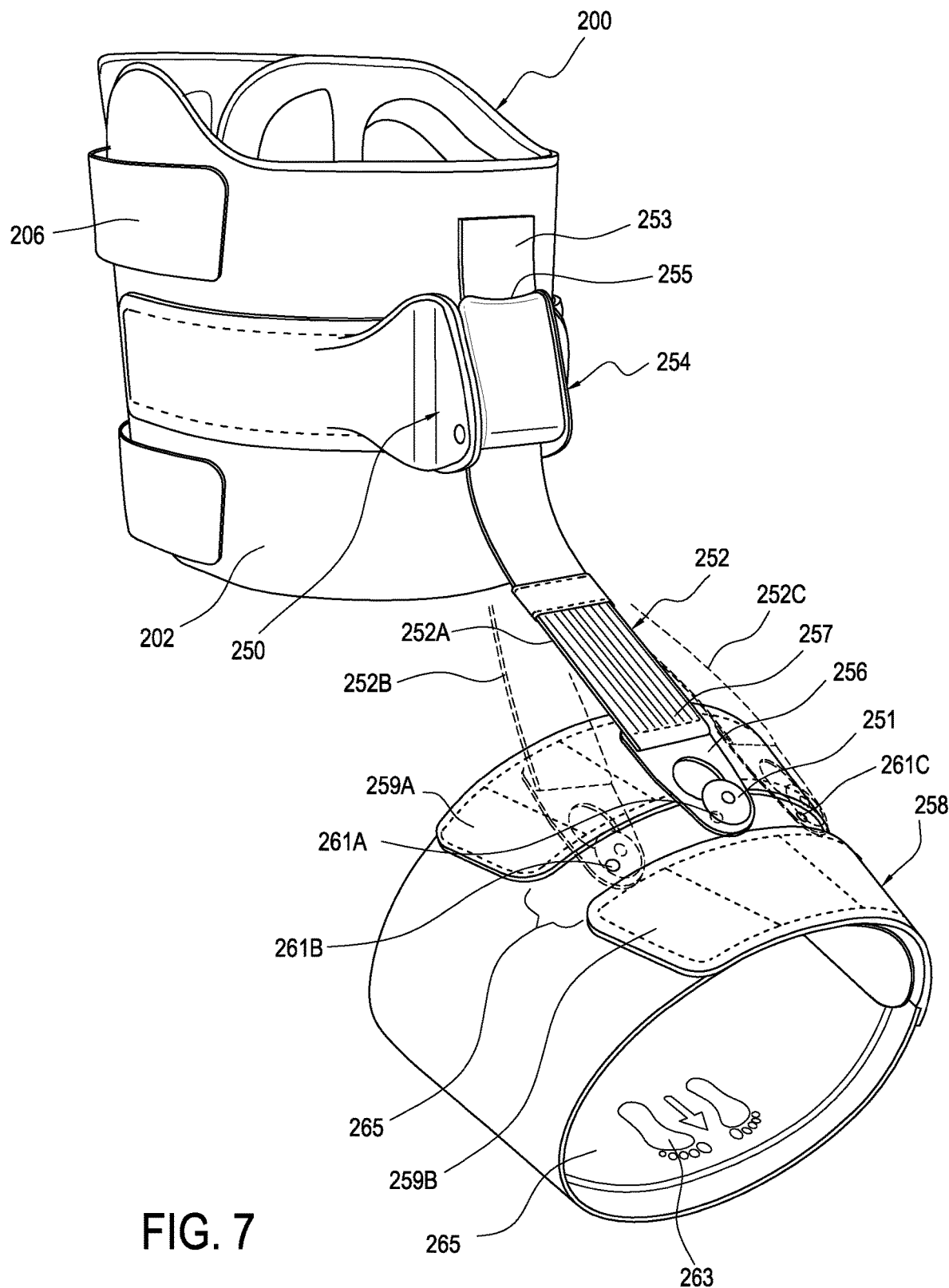
FIG. 7 is a perspective view of an orthopedic device including the ankle component of FIG. 4 secured to the ankle and foot of a user.

FIG. 7 shows the ankle component 200 of FIG. 4 with an attachment component 250 coupling to a strap assembly 252 connected to a foot component 258. The attachment component 250 includes a lever device 254 that serves as a buckle for grasping a first portion of the strap assembly 252 and maintaining a length of the strap assembly 252 extending therefrom. A coupling part 256 extends from a second portion of the strap assembly 252, preferably at a second end thereof. As discussed in following embodiments, the strap assembly 252 may have a pull tab 253 for adjusting the strap assembly 252 relative to the lever device 254.

Advantageously, the foot component 258 defines a plurality of apertures 261A, 261B, 261C to allow for the attachment component 250 to be arranged for enhanced medial or lateral control, and thereby place the anchor and strap assembly 252 in an offset orientation relative to a neutral orientation. An anchor 251, which may resemble the anchor 174 in FIG. 16, may be selectively attached the foot component 258 via any of the apertures 261A, 261B, 261C formed by the foot component 258, and the coupling part 256 may couple to anchor 174, as disclosed in other embodiments disclosed herein or by other known means.

As exemplified in FIG. 7, the strap assembly 252 may be orientated at an angle relative to a center of a leg. The first or center aperture 261A, may correspond to neutral orientation or central control to offer dynamic support for drop foot or other related disorders that require dorsiflexion. In the orientation 252A of the strap assembly, the support to the foot and ankle is neutral. A second aperture 261B may be on either the lateral or medial side of the foot and relative to the first or center aperture 261A for increased lateral or medial control. In this manner, the orientation 252B of the strap assembly is offset to the neutral orientation and offers more stability on the prescribed side of the foot upon which the aperture is located, or in other words the side of the center aperture 261A at which the second aperture 261B is located. The third aperture 261C is preferably on an opposite side of the center aperture 261A than the second aperture 261B, and offers enhanced support from that side of the foot with the orientation 252C of the strap assembly.

The foot component 258 is preferably a wrap including a body portion 257 including at least one strap 259A, 259B extending from the body portion 257. As shown, there are two straps 259A, 259B that are spaced apart from one another to create a clearance therebetween which exposes the apertures 261A, 261B, 261C formed through the body portion 257, so that the straps 259A, 259B can be adjusted without interfering or covering the apertures 261A, 261B, 261C. The foot component 258 preferably forms a tubular structure that can be comfortably and flexibly applied about a foot. The at least one strap 259A, 259B and the body portion 257 may be arranged similarly as the main support 102 whereby the at least one strap 259A, 259B is readily secured over the entirety of the surface of the main support 102. The interior portion 265 may define indicia 263 illustrating directions and locations for orienting and applying the foot component 258 about the foot of a wearer, to make the foot component more intuitive for donning.

The foot component 258 may be formed from a foam laminated with nylon/spandex and loop. The foot component 258 can be wearable under clothing, and has an anatomical shape to fit most walking shoes. As described below regarding FIG. 15, a footwear or shoe S alone may qualify as a foot component itself with the anchor being selectively located and secured on the footwear.

FIGS. 8A and 8B depict an embodiment of an attachment component 260. The attachment component 260 includes lateral wings 262A, 262B that extend laterally from a lever 266. The lateral wings 262A, 262B each define an elongate slot 264 arranged for enabling better flexibility and breathability of the wings. The lever 266 is arranged to bias against a base 274 of the attachment component 260, with preferably a strap assembly located therebetween (as shown in FIG. 7). The lever 266 and the base 274 define a channel 270 located therebetween in which a wedge 272 of the lever 266 can be urged against the strap assembly to maintain a length of the strap assembly extending from the attachment component. As shown, the lever 266 is pivotally secured to the base 274 by pins 276 and comprises handle 268.

FIGS. 9A-9C exemplify another attachment component in the form of a buckle 280 attached directly to the ankle component 200 and the strap assembly 252. Specifically, the buckle 280 includes a frame 282 and a lever 284 pivotally attached to the frame 282 by pins 290. The lever 284 and biased thereagainst by a spring 286 within an opening 288 formed by the frame 282. The spring 286 attaches at a first end to a bar 296 of the frame 282, and to the spring 286 at a second end. In a biased position, teeth 294 formed by or included on the lever 284 are urged against a biasing surface 292 formed by the frame 282 for clamping the strap assembly and maintaining in length.

In an embodiment depicted in FIG. 9D, lever 284 comprises a logarithmic curve profile 273 at a periphery of wedge 272. The logarithmic curve profile 273 improves upon existing strap attachment and adjustment devices which generally comprise levers having flat profiles. The logarithmic curve profile 273 mitigates the problem of strap force components creating a clearance between the base 282 and the lever 284, which leads to unwanted slippage of the strap. The problem is mitigated by the logarithmic curve profile 273 of the lever 284 providing an improved force profile relative to the strap assembly 252, advantageously reducing slippage. In a preferred embodiment, lever 284 cooperates with sloped portion 295 and teeth 294 to more securely hold a strap in place than existing levers which comprise flat profiles. Lever 284 and sloped portion 295 define a portion of a channel 271 through which a strap may be configured to pass. The logarithmic curve profile 273 and/or sloped portion 295 may advantageously be adapted for use with any of the embodiments heretofore or hereafter mentioned.

A user can adjust a length of the strap assembly 252 between the buckle 280 and the foot by pressing the lever 284 to disengage from the strap assembly 252, and then release the lever 284 once the desired length is determined at which point the spring 286 biases the lever 284 against the strap assembly 252. This method of operation makes it so the strap assembly 252 is adjustable with a single hand, and the ankle component 200 stays in place on the ankle when the strap assembly 252 is tightened. The buckle 280 enables length adjustment of the strap, and permits easy replacement of the strap if it becomes worn or no longer effective. The buckle also allows the universal use of a wrap-type foot component (as in FIG. 7) or an inlay or mounting element (as in FIG. 12), or other mounting means described herein to the foot of a user.

Figure 10:
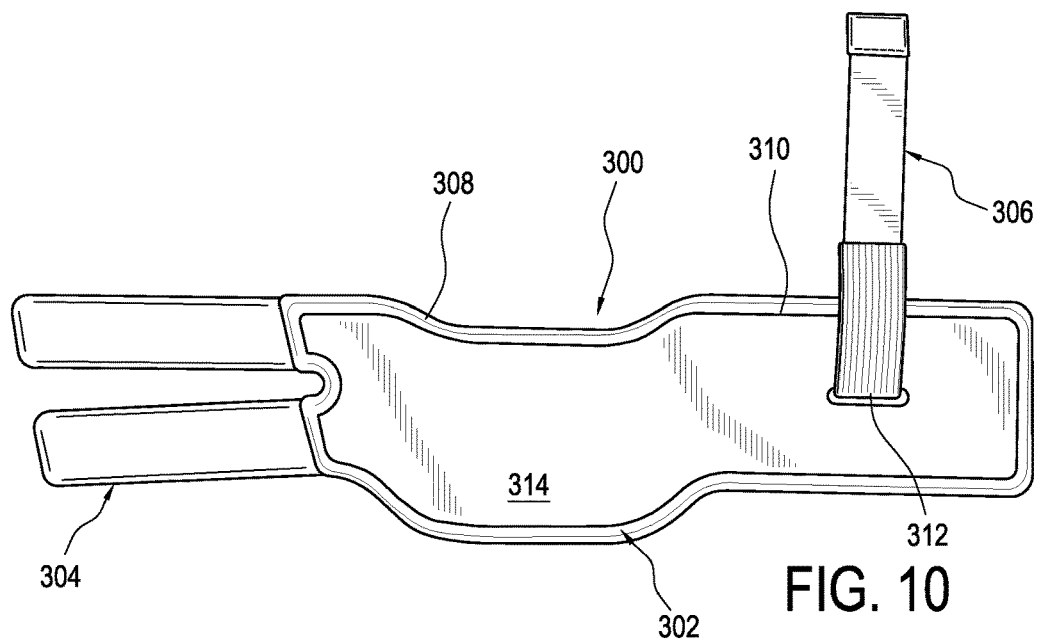
FIG. 10 is a plan view of another embodiment of an ankle component in a flat, non-contoured configuration showing an outer side.
Figure 11:
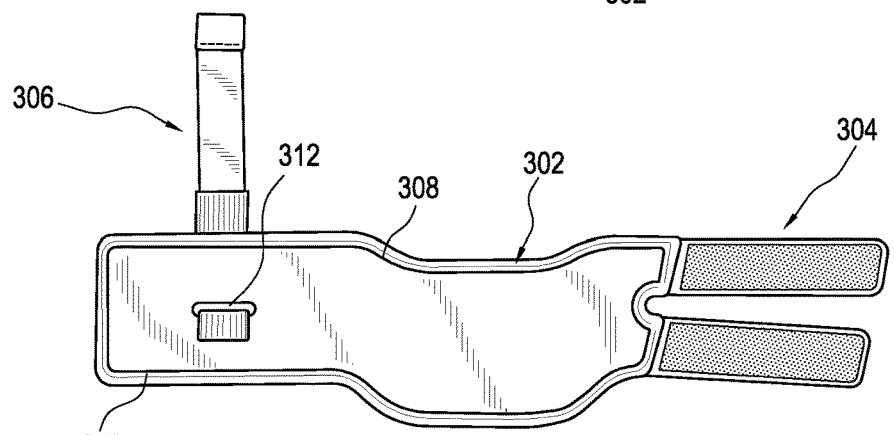
FIG. 11 is a plan view of the ankle component of FIG. 10 showing an inner side.

FIGS. 10 and 11 disclose an embodiment of a foot component 300 adapted as a shoeless version of a drop foot orthoses. In this embodiment, the foot component 300 includes a body 302 having a main section 308 and a wing section 310. The main section 308 is adapted to extend about the sole of the user's foot, and the wing section 310 is adapted to wrap about the top of the foot in combination with at least one strap 304 extending from the main section 310. The at least one strap 304 is adapted to secure over an outer surface 314 of the body 302. The strap assembly 306 is secured to the wing section 310. The method of securing the strap assembly 306 to the wing section 310 may be a slit 312 through which the strap assembly secures or slides through. Alternative methods for securing the strap assembly 306 to the wing section 310 are described in FIGS. 17, 18 and 19. The ankle component 300 may include similar or any of the features discussed with the embodiment of FIGS. 4 and 5, inclusive the padding, thermoforming, traction features, layers, debossed segment, and connection with a buckle or attachment component.

Figure 12:
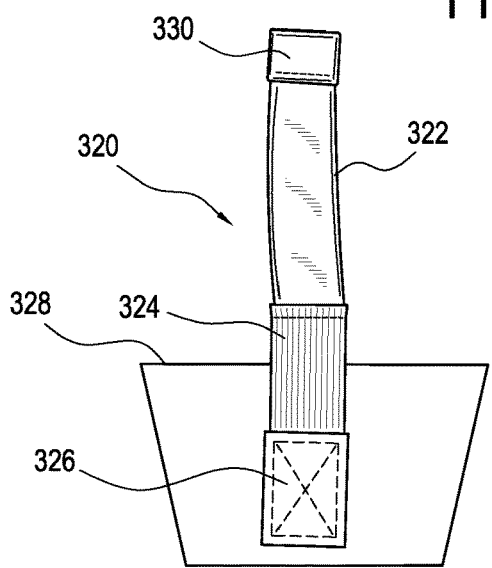
FIG. 12 is a plan view showing an embodiment of a strap assembly for use with the ankle component of FIG. 10.

FIG. 12 depicts an embodiment of a strap assembly 320 includes a mounting element 328, such a flexible inlay. The strap assembly 320 includes a main segment 322 and at least one elastic segment 324 secured directly to the main segment 322. The at least one elastic segment 324 may include two elastic segments 324 parallel and generally coextensive with one another for improved stretchability and control of the strap assembly 320, when tensioned. A pull tab 330 is at a first end of the strap assembly 320 and preferably directly secured to the main segment 322, and a securing tab 326 is preferably directly secured to the mounting element 328. An advantage to the elastic segment 324 is that it gives support during the swing phase by accommodating the movement between the foot and the ankle, and allows for voluntary plantar flexion (as opposed to an inelastic segment that does not permit articulation). The elastic connection is adjustable between ankle and a foot component.

Figure 13:
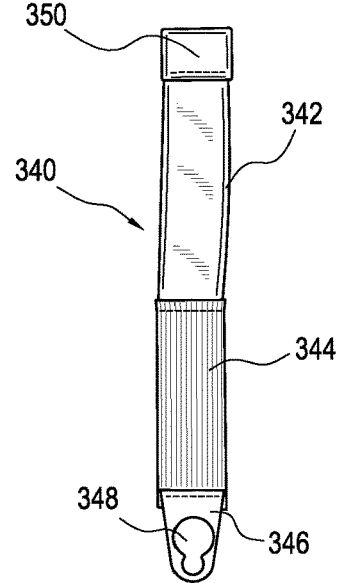
FIG. 13 is a plan view showing another embodiment of a strap assembly for use with the ankle component of FIG. 10.

FIG. 13 illustrates another embodiment of a strap assembly 340 likewise including a main segment 342, at least one elastic segment 344, and a pull tab 350. The strap assembly 340 has a coupling part 346 defining a keyhole 348 opening for securing to an anchor mountable onto a shoe, an anchoring assembly, or a foot component, as discussed in combination with the embodiments of FIGS. 14A-20B.

Figure 15:
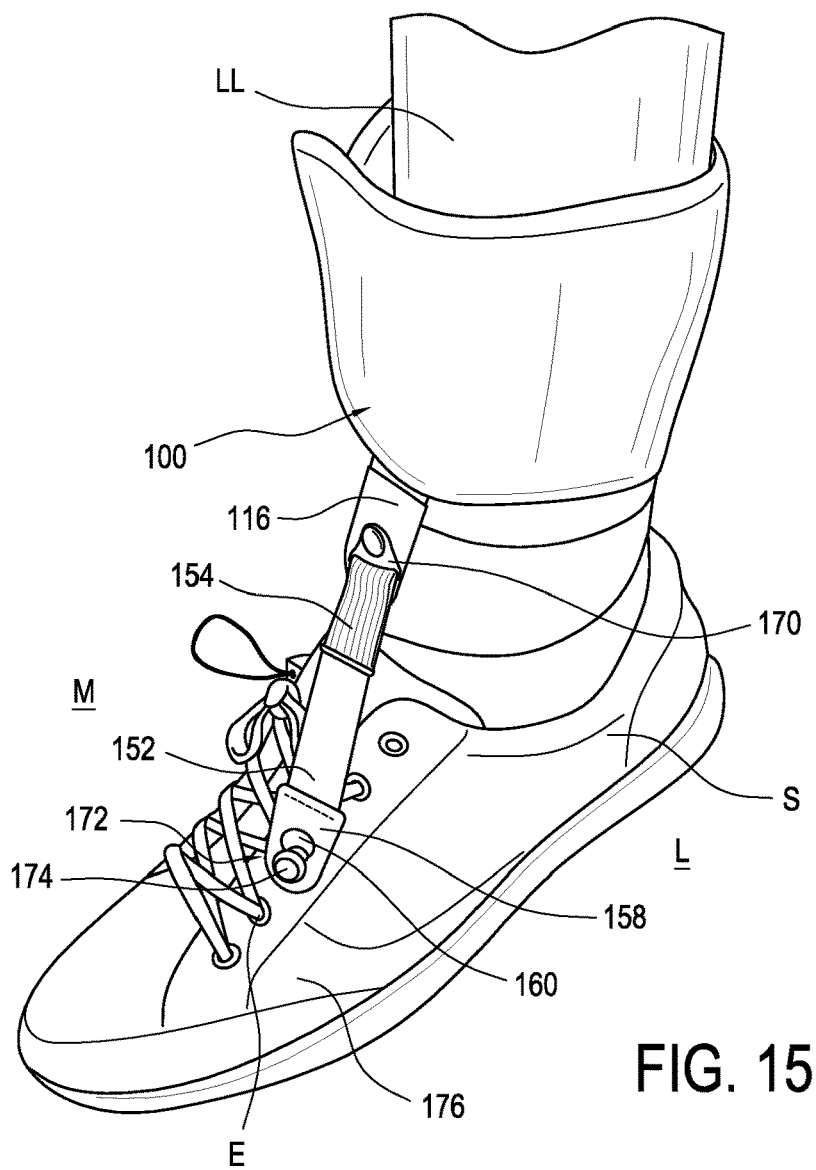
FIG. 15 is a schematic view of the orthopedic device on an ankle and shoe of a user.

Referring to FIGS. 14A and 14B, the orthopedic device 100 includes a strap assembly 150 extending from the ankle component 102 to an anchor 174 for securing to a shoe (as shown in FIG. 15), or a foot component (as described above). The strap assembly 150 preferably includes at least one elastic segment 152 that connects at a first end to a securing tab 158 defining a keyhole 160, and at a second end to main segment 154. The inelastic strap segment 154 secures to a buckle 156 adapted for coupling to the strap attachment 112 on the main support 102. The buckle 156 has a ratcheting handle 162 adapted to permit the user to adjust the length of the strap assembly, particularly the inelastic strap body 154.

In the embodiment of FIG. 14A, the buckle 156 replaces the strap attachment 112 depicted in the embodiment of FIGS. 2 and 3, as the buckle 156 is mounted on the main support 102. The buckle 156 preferably includes a ratcheting device for winding the inelastic strap body 152 thereabout for resizing the length of the strap assembly 150.

FIG. 15 depicts the orthopedic device 100 secured to the lower leg LL and the shoe S of the user. A shoe attachment system 172 includes the anchor 174 secured to an eyelet E of the user's shoe S. In this embodiment, footwear or shoe S is worn without the aforementioned foot component, and the footwear or shoe S itself qualifies as a foot component for receiving and selective placement of the anchor 174. In the embodiment of FIG. 15, attachment tab 170 attaches strap body 152 to buckle 116.

Figure 16:
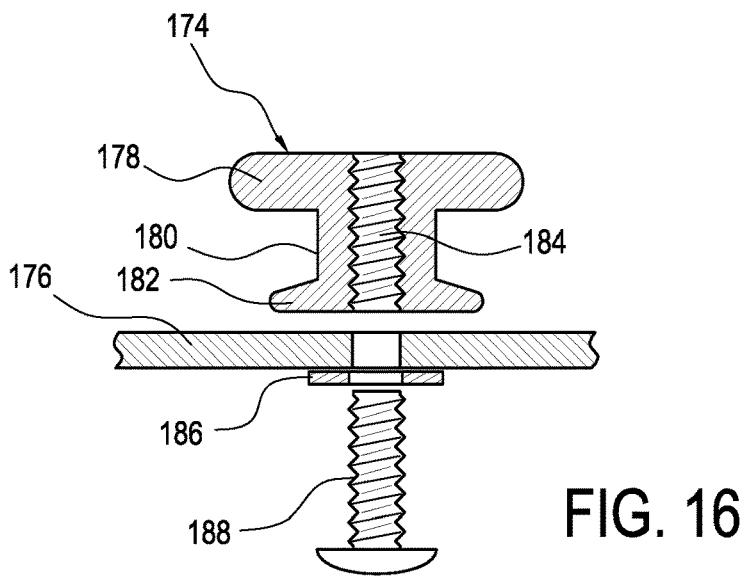
FIG. 16 is a schematic view of an anchor assembly in FIG. 15 for coupling to a shoe.

FIG. 16 depicts an embodiment of the anchor 174 arranged in a nut-and-bolt construction. The anchor includes a first head 178 for extending above or outside the shoe or foot component. A shaft 180 extends from the first head 178 to a second head 182, adapted to rest above a layer or thickness of a first side 176 of a shoe or foot component. The shaft 180 defines an internal thread 184 into which a screw 188 engages and passes through a washer 186 arranged for abutting against a second side of a shoe.

In use, the anchor 174 is installed in a shoe eyelet E, either on a lateral L or medial M side of the shoe, providing the user lateral or medial control. The terms medial and lateral have their generally understood meanings, particularly in regard to footwear. Specifically, medial means towards the middle of the body or inside of the foot, and lateral means towards the outside of the body or outside of the foot. The anchor 174 may be secured to a foot component, as depicted in FIGS. 10 and 11, through an eyelet in the wing section 310. The wing section 310 may have a plurality of eyelets positioned from the medial to the lateral side. The user may have more lateral or more medial support from the device, depending on which eyelet is chose.

A plate as in the prior art may be provided under the laces with an anchor provided thereon for securing to the tab 158 of the strap assembly 150. The main support 102 is wrapped about the lower leg LL with the straps and main support 102 combining to circumferentially extend about the lower leg LL, preferably with the supplemental support 114 about the Achilles heel. The strap assembly 150 is drawn from the main support 102 once installed upon the lower leg LL and against the elasticity of the strap body 152, and secured about the anchor 174.

Figure 17:
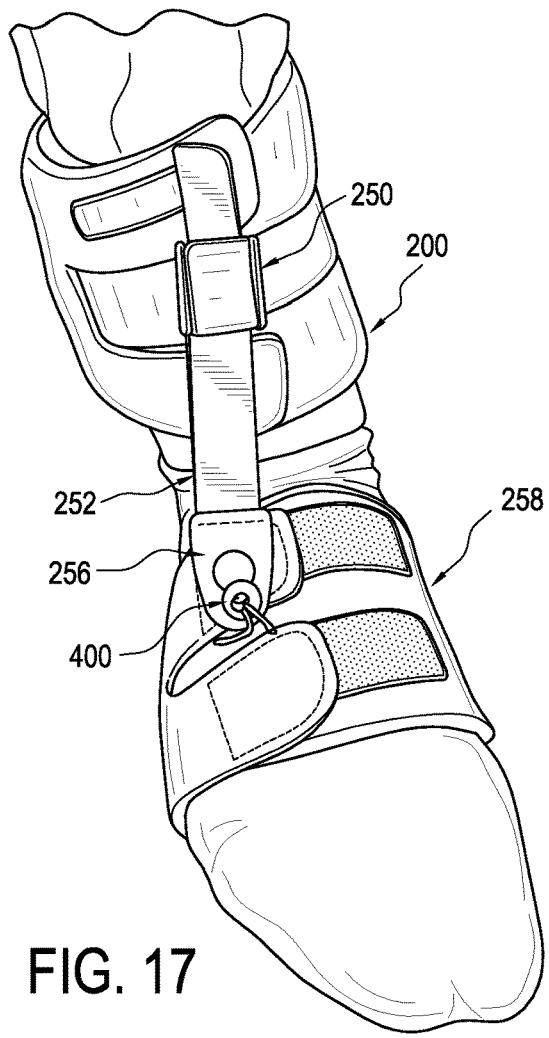
FIG. 17 is a schematic perspective view of a variation of the orthopedic device of FIG. 7 secured to the ankle and foot of a user.

FIG. 17 depicts the ankle component 200 of FIG. 4 coupled to a foot component 258 by the strap assembly 252 and adjusted by the attachment component 250. The coupling part 256 engages an anchor 400 carried by the foot component 258. The arrangement in FIG. 17, unlike in the embodiment of FIG. 15, enables the orthopedic device to be worn without shoes.

Figure 18:
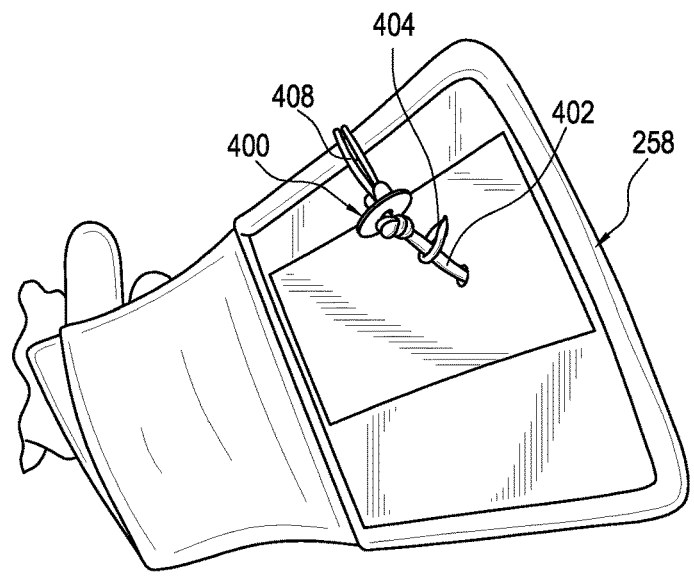
FIG. 18 is a partial perspective view of the foot component of FIG. 17.

FIG. 18 depicts the anchor 400 as being connected to the foot component 258 because a cable 402 extends from the foot component 258 and is maintained by a retainer 404. The cable 402 may be arranged to be tied at an end 408 so the length of the cable 402 or segment thereof carrying the anchor 400 may be adjustable depending on the user's requirements.

Figure 19:
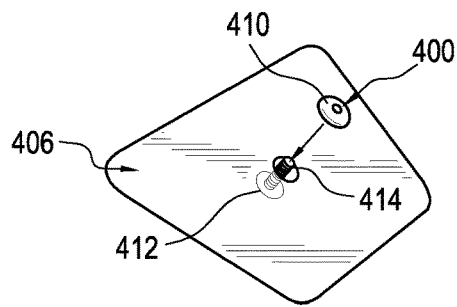
FIG. 19 is a perspective view of an inlay assembly for securing to a shoe.

FIG. 19 shows an embodiment of an anchor 400 attached to an inlay or mounting plate 406. The anchor 400 includes a fastener 412 having a shaft for extending through an aperture 414 defined by the inlay 406 and receiving a cap 410. The cap 414 is arranged for extending above the inlay 406 to permit securing to the coupling part in other views. The inlay 406 has a shape with a flared first region and a narrower second region to make it intuitive for donning because the shape generally conforms to a general shape of a foot, with the second portion closer to the toes, and the first portion closer to the leg.

Figure 20A:
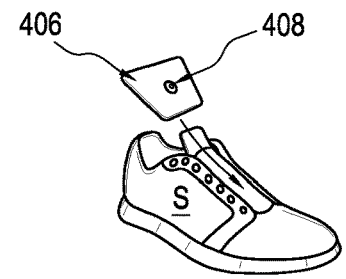
FIGS. 20A and 20B are a schematic view of steps for securing the inlay assembly into a shoe.
Figure 20B:
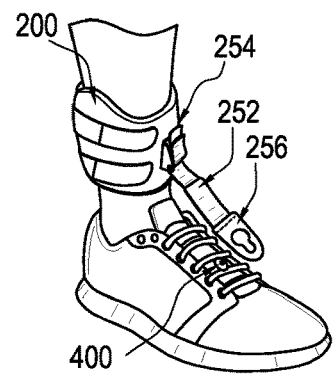

FIG. 20A illustrates how the inlay 406 is inserted into the instep of a shoe and below laces. FIG. 20B depicts the ankle component 200 as coupled to the strap assembly 252 adjusted by the attachment component 252. The coupling part 256 is placed over the anchor 400 protruding through the laces or from the shoe.

It is to be understood that not necessarily all objects or advantages may be achieved under any embodiment of the disclosure. Those skilled in the art will recognize that the orthopedic device may be embodied or carried out in a manner that achieves or optimizes one advantage or group of advantages as taught herein without necessarily achieving other objects or advantages as taught or suggested herein.

The skilled artisan will recognize the interchangeability of various disclosed features. Besides the variations described, other known equivalents for each feature can be mixed and matched by one of ordinary skill in this art to construct an orthopedic device under principles of the present disclosure. It will be understood by the skilled artisan that the features described may be adapted to other types of orthopedic devices. Hence this disclosure and the embodiments and variations thereof are not limited to knee braces, but can be utilized in any orthopedic devices.

Although this disclosure describes certain exemplary embodiments and examples of an orthopedic device, it therefore will be understood by those skilled in the art that the present disclosure extends beyond the specifically disclosed knee brace embodiments to other alternative embodiments and/or uses of the disclosure and obvious modifications and equivalents thereof. It is intended that the present disclosure should not be limited by the particular disclosed embodiments described above, and may be extended to orthopedic devices and supports, and other applications that may employ the features described herein.

The invention claimed is:

1. An orthopedic device, comprising:
   a main support adapted to secure about a lower leg, wherein the main support defines a curved shape having a semi-rigid or rigid form, and arranged to resiliently maintain the curved shape between donning and doffing of the orthopedic device;
   at least one strap extending from the main support and arranged to wrap about an ankle;
   a strap assembly having a first portion coupling to the main support, and a second portion arranged to be drawn therefrom, the strap assembly including a main segment and at least one elastic segment attached to the main segment, the strap assembly located between the first and second portions, the main segment being less elastic than the at least one elastic segment and including the first portion;
   an anchor for receiving and attaching to the second portion of the strap assembly;
   an attachment component secured to the main support the first portion of the strap assembly coupling to the attachment component, the attachment component including a base and lateral wings extending laterally from the base over the main support and forming the curved shape of the main support, the base being centrally located on the main support at an apex of the curved shape thereof.

2. The orthopedic device of claim 1, further comprising a foot component upon which the anchor is positioned.

3. The orthopedic device of claim 2, wherein the foot component defines at least two apertures among which the anchor is selectively secured to the foot component.

4. The orthopedic device of claim 2, wherein the foot component includes at least two straps extending from a main portion of the foot component, the at least two straps defining a clearance therebetween and over the main portion at which the anchor is secured.

5. The orthopedic device of claim 1, wherein the strap assembly is releasably attached to the anchor and adjustable in length at the first portion relative to the main support.

6. The orthopedic device of claim 1, wherein the attachment component comprises a lever arranged to bias against the base and to grasp the first portion of the strap assembly, the lever and the base defining a channel therebetween in which a wedge of the lever is urged against the strap assembly, the lever having a substantially logarithmic curve profile.

7. The orthopedic device of claim 6, wherein an end of the first portion defines a tab extending from a first end of the attachment component, and the first portion extends through the lever and from a second end of the lever device towards the anchor.

8. The orthopedic device of claim 6, wherein the base defines a sloped portion and the lever defines teeth proximate the channel.

9. The orthopedic device of claim 1, wherein the main segment has a first end from which a tab extends and a second end at which a first end of the at least one elastic segment secures.

10. The orthopedic device of claim 1, wherein a second end of the at least one elastic segment carries a coupling part securable to the anchor.

11. The orthopedic device of claim 10, wherein the coupling part defines a keyhole adapted to receive a head of the anchor and engage a shaft extending from the head due to bias of the at least one elastic segment pulling the coupling part toward the leg support.

12. An orthopedic device, comprising:
    a main support adapted to secure about a lower leg, wherein the main support defines a curved shape having a semi-rigid or rigid form, and arranged to resiliently maintain the curved shape between donning and doffing of the orthopedic device;
    at least one strap extending from the main support and arranged to wrap around an ankle;
    a strap assembly having a first portion coupling to the main support, and a second portion arranged to be drawn therefrom, the strap assembly including a main segment and at least one elastic segment attached to the main segment, the strap assembly located between the first and second portions, the main segment being less elastic than the at least one elastic segment and including the first portion;
    a foot component adapted to secure about a foot;
    an anchor for receiving and attaching to the second portion of the strap assembly and selectively positioned on a foot component, wherein the anchor is adjustable from a relative to a neutral strap assembly orientation to an offset orientation, such that the strap assembly extends at a non-parallel angle between the main support and the anchor relative to the neutral orientation;

an attachment component secured to the main support the first portion of the strap assembly coupling to the attachment component, the attachment component including a base and lateral wings extending laterally from the base over the main support and forming the curved shape of the main support, the base being centrally located on the main support at an apex of the curved shape thereof.

13. The orthopedic device of claim 12, wherein the attachment component comprises a lever arranged to bias against the base and to grasp the first portion of the strap assembly, the lever and the base defining a channel therebetween in which a wedge of the lever is urged against the strap assembly, the lever having a substantially logarithmic curve profile.

14. The orthopedic device of claim 13, wherein the base defines a sloped portion and the lever defines teeth proximate the channel.

* * * * *